US00PP23562P2

(12) United States Plant Patent
Smith

(10) Patent No.: US PP23,562 P2
(45) Date of Patent: Apr. 23, 2013

(54) ***CHRYSANTHEMUM* PLANT NAMED 'CIFZ0002'**

(50) Latin Name: *Chrysanthemum×morifolium*
Varietal Denomination: CIFZ0002

(75) Inventor: Mark A. Smith, Alva, FL (US)

(73) Assignee: Syngenta Crop Science Protection AG, Basel (CH)

( * ) Notice: Subject to any disclaimer, the term of this patent is extended or adjusted under 35 U.S.C. 154(b) by 0 days.

(21) Appl. No.: 13/385,185

(22) Filed: Feb. 6, 2012

(51) Int. Cl.
*A01H 5/00* (2006.01)

(52) U.S. Cl. ..... Plt./293

(58) Field of Classification Search ..... Plt./293
See application file for complete search history.

*Primary Examiner* — Annette Para
(74) *Attorney, Agent, or Firm* — Joshua L. Price

(57) ABSTRACT

A new *Chrysanthemum* plant named 'CIFZ0002' particularly distinguished by the small red decorative inflorescences, yellow-green foliage, medium ball-shaped plant habit, and a natural flowering season response of late September.

1 Drawing Sheet

Latin name of the genus and species of the plant claimed: *Chrysanthemum×morifolium.*

Varietal denomination: 'CIFZ0002'.

BACKGROUND OF THE NEW PLANT

The present invention comprises a new *Chrysanthemum*, botanically known as *Chrysanthemum×morifolium*, and hereinafter referred to by the variety name 'CIFZ0002'.

'CIFZ0002' is a product of a planned breeding program. The new cultivar has small red decorative inflorescences, yellow-green foliage, medium ball-shaped plant habit, and a natural flowering season response of late September.

'CIFZ0002' originates as a natural whole plant mutation of an unpatented variety designated '05-M166'. 'CIFZ0002' was discovered and selected by the inventor as a single flowering plant within a large population of the parent cultivar, grown massed in pots outdoors in a controlled breeding program in Alva, Fla. in April 2008. The parent cultivar '05-M166' has purple inflorescence color, similar plant size and habit, with a natural season flowering response that is a few days slower than 'CIFZ0002'.

The first act of asexual reproduction of 'CIFZ0002' was accomplished when vegetative cuttings were propagated from the initial selection in May 2008 in a greenhouse in Alva, Fla.

BRIEF SUMMARY OF INVENTION

Horticultural examination of plants grown from cuttings of the plant initiated in May 2008, and continuing thereafter, has demonstrated that the combination of characteristics as herein disclosed for 'CIFZ0002' are firmly fixed and are retained through successive generations of asexual reproduction.

'CIFZ0002' has not been observed under all possible environmental conditions. The phenotype may vary significantly with variations in environment such as temperature, light intensity, and day length.

Plant Breeder's Rights for this cultivar were applied for in Canada on Feb. 24, 2011, No. 11-7176 and in the Community Plant Variety Office on Mar. 30, 2011, No. 2011/0787.

'CIFZ0002' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0002' with colors being as true as possible with an illustration of this type. The photographic drawing shows a flowering potted plant of the new variety and a close-up of the flowers.

DETAILED BOTANICAL DESCRIPTION

The plant descriptions, measurements and aforementioned close-up photograph were collected and/or taken outdoors in Gilroy, Calif. in early November 2011. These plants were grown outdoors in gallon pots and were approximately 12 weeks of age.

The aforementioned photograph of the whole plant was taken in later September 2011 in Monroeville, N.J. and plants were about 15 weeks old, grown outdoors.

Color references are made to The Royal Horticultural Society Colour Chart (R.H.S.) 2001.

TABLE 1

DIFFERENCES BETWEEN THE NEW VARIETY 'CIFZ0002' AND A MOST SIMILAR VARIETY

| | 'CIFZ0002' | 'Gedi One Sav' (U.S. Plant Pat. No. 13,928) |
|---|---|---|
| Inflorescence diameter: | Smaller | Larger |
| General plant size: | Smaller | Larger |
| Black cloth and natural flowering season response: | Faster | Slower |

Plant:
*Form, growth and habit*.—Herbaceous garden-type, stems upright and outwardly spreading, freely branching.
*Plant height*.—12.0-13.0 cm.
*Plant height* (*inflorescence included*).—14.0-15.0 cm.
*Plant width*.—22.0-24.0 cm.
Roots:
*Number of days to initiate roots*.—About 4 days at about 22 degrees C.
*Number of days to produce a rooted cutting*.—4-6 days at 22 degrees C.
*Type*.—Fine, fibrous, free branching.
*Color*.—RHS N155B but whiter.
Foliage:
*Arrangement*.—Alternate.
*Immature, leaf color, upper surface*.—RHS 147A but a little lighter.
*Lower surface*.—Closest to RHS 147B.
*Mature, leaf color, upper surface*.—Closest to RHS 147A.
*Lower surface*.—Closest to RHS 147B.
*Length*.—3.1-3.4 cm.
*Width*.—3.0-3.1 cm.
*Shape*.—Ovate.
*Base shape*.—Attenuate.
*Apex shape*.—Mucronulate.
*Margin*.—Palmately lobed, irregularly incised, serrate.
*Texture, upper surface*.—Bifid T-shaped hairs.
*Lower surface*.—Bifid T-shaped hairs.
*Color of veins, upper surface*.—RHS 138B.
*Color of veins, lower surface*.—RHS 138B.
*Petiole color*.—RHS 138B.
*Length*.—0.8-1.2 cm.
*Diameter*.—0.2 cm.
*Texture*.—Bifid T-shaped hairs.
Stem:
*Quantity of main branches per plant*.—About 10.
*Color of stem*.—RHS 138A, but appears lighter due to the hairs.
*Length of stem*.—6.0-7.0 cm.
*Diameter*.—0.25-0.3 cm.
*Length of internodes*.—0.7-1.0 cm.
*Texture*.—Bifid T-shaped hairs.
*Color of peduncle*.—RHS 138B but appears lighter due to the hairs.
*Length of peduncle*.—3.5-5.0 cm.
*Peduncle diameter*.—0.1 cm.
*Texture*.—Bifid T-shaped hairs.
Inflorescence:
*Type*.—Compositae, solitary decorative-type inflorescences; borne terminally above foliage, ray florets arranged acropetally on a capitulum.
*Quantity of inflorescences per plant*.—About 125.
*Lastingness of individual blooms on the plant*.—A little less than 6 weeks from first color showing.
*Fragrance*.—Slightly spicy.
Bud (just when opening/showing color):
*Color*.—RHS 184A.
*Length*.—0.9-1.1 cm.
*Width*.—0.8-0.9 cm.
*Shape*.—Oblate.
Immature inflorescence:
*Diameter*.—2.0-2.5 cm.
*Color of ray florets, upper surface*.—Closest to RHS 53A.
*Lower surface*.—RHS 182A.
Mature inflorescence:
*Diameter*.—3.1-3.5 cm.
*Depth*.—1.5 cm.
*Total diameter of disc*.—0.1-0.2 cm.
*Receptacle height*.—0.3 cm.
*Receptacle diameter*.—0.35.
Ray florets:
*Average quantity of florets*.—About 90 in several whorls.
*Color of florets, upper surface*.—RHS 53A, maturing to RHS 185B.
*Lower surface*.—Closest to RHS 182A maturing to about RHS 182C.
*Length*.—1.1 cm.
*Width*.—0.3-0.4 cm.
*Shape*.—Oblong.
*Apex shape*.—Praemorse.
*Margin*.—Entire.
*Texture, upper surface*.—Papillose.
*Lower surface*.—Papillose.
Disc florets:
*Average quantity of florets*.—13-22.
*Color of florets*.—RHS 155C with RHS 6C apex.
*Length*.—0.3-0.4 cm.
*Width*.—0.1 cm.
*Shape*.—Tubular, elongated.
*Apex shape*.—Acute, 5 pointed.
Phyllaries:
*Quantity*.—About 35.
*Color, upper surface*.—RHS 144A.
*Lower surface*.—RHS 138A.
*Length*.—0.5 cm.
*Width*.—0.15 cm.
*Shape*.—Lanceolate.
*Apex shape*.—Acute.
*Base*.—Fused.
*Margins*.—Entire; some are papery with RHS 200B margins.
*Texture, upper surface*.—Glabrous.
*Lower surface*.—Bifid T-shaped hairs.
Reproductive organs:
*Pistil*.—1, found on both types of florets.
*Length*.—0.4-0.5 cm.
*Style color*.—RHS 155C.
*Style length*.—0.3-0.4 cm.
*Stigma color*.—RHS 6C.
*Stigma shape*.—Bi-parted.
*Ovary color*.—RHS 155C.
*Ovary length*.—0.1 cm.
*Ovary width*.—0.05 cm.
*Stamens*.—4, found on only on the disc florets.
*Color of filaments*.—RHS 155C.
*Length filaments*.—0.2-0.3 cm.
*Anther color*.—RHS 15C.
*Anther length*.—0.1 cm.
*Anther shape*.—Oval.
*Pollen amount*.—None found.

What is claimed is:

1. A new and distinct variety of *Chrysanthemum* plant named 'CIFZ0002' substantially as illustrated and described herein.

* * * * *

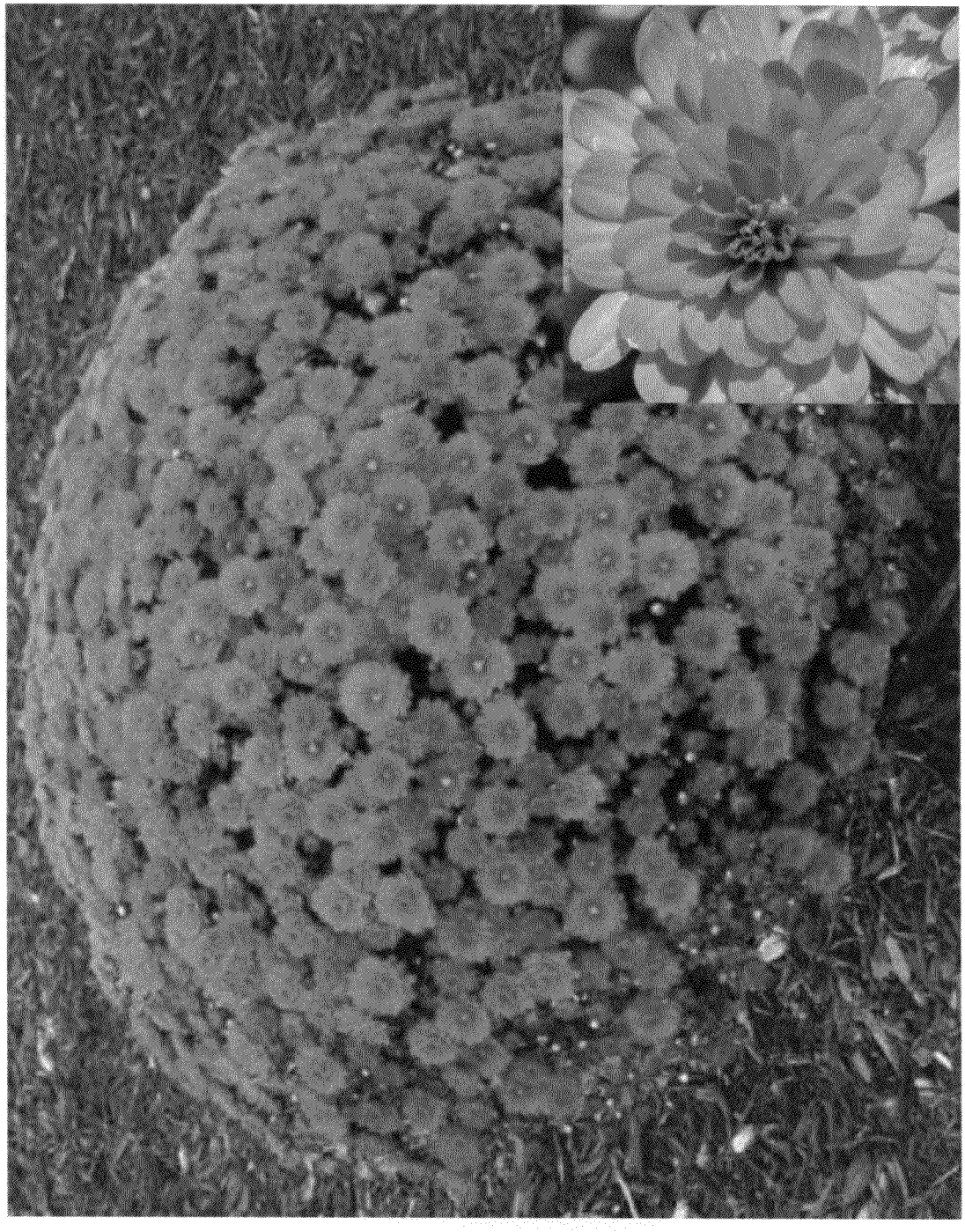

UNITED STATES PATENT AND TRADEMARK OFFICE

CERTIFICATE OF CORRECTION

PATENT NO. : PP23,562 P2
APPLICATION NO. : 13/385185
DATED : April 23, 2013
INVENTOR(S) : Smith It is certified that error appears in the above-identified patent and that said Letters Patent is hereby corrected as shown below:

Title Page, Item (73) Assignee:, delete "Syngenta Crop Science Protection AG, Basel (CH)" and insert therefor --Syngenta Crop Protection AG, Basel (CH)--

In the Specification

At column 4, line 6, delete "0.35" and insert therefor --0.35 cm--

Signed and Sealed this
Eighteenth Day of June, 2013

Teresa Stanek Rea

Teresa Stanek Rea
*Acting Director of the United States Patent and Trademark Office*